(12) United States Patent
Jaccard

(10) Patent No.: US 7,824,352 B2
(45) Date of Patent: Nov. 2, 2010

(54) AMBIDEXTROUS WRIST BRACE WITH THUMB IMMOBILIZER

(75) Inventor: Jean-Patrick Jaccard, Caslano (CH)

(73) Assignee: Sports & Supports Limited, Dublin (IE)

( * ) Notice: Subject to any disclaimer, the term of this patent is extended or adjusted under 35 U.S.C. 154(b) by 303 days.

(21) Appl. No.: 12/092,270

(22) PCT Filed: Oct. 18, 2006

(86) PCT No.: PCT/EP2006/010035

§ 371 (c)(1),
(2), (4) Date: May 1, 2008

(87) PCT Pub. No.: WO2007/051524

PCT Pub. Date: May 10, 2007

(65) Prior Publication Data

US 2008/0287848 A1    Nov. 20, 2008

(30) Foreign Application Priority Data

Nov. 2, 2005  (IT) ................... MI2005A2085

(51) Int. Cl.
*A61F 5/00* (2006.01)
(52) U.S. Cl. .................................... 602/20; 602/21

(58) Field of Classification Search ............. 602/20–23; 128/877–879

See application file for complete search history.

(56) References Cited

U.S. PATENT DOCUMENTS

| | | | | |
|---|---|---|---|---|
| 5,000,195 | A | * | 3/1991 | Neal ............................ 602/27 |
| 5,695,453 | A | * | 12/1997 | Neal ............................ 602/6 |
| 5,899,870 | A | | 5/1999 | Deirmendjian et al. |
| 6,142,966 | A | | 11/2000 | Hely |
| 6,893,410 | B1 | | 5/2005 | Hely |
| 2003/0191421 | A1 | | 10/2003 | Weaver, II et al. |
| 2004/0049141 | A1 | * | 3/2004 | Slautterback et al. ......... 602/21 |
| 2007/0225630 | A1 | * | 9/2007 | Wyatt et al. ................... 602/21 |

* cited by examiner

*Primary Examiner*—Michael A. Brown
(74) *Attorney, Agent, or Firm*—Young & Thompson

(57) ABSTRACT

An ambidextrous wrist brace is described, having a substantially rectangular main strap (2) designed to be closed in a tubular shape around the wrist and provided with a slot (21) through which the user's thumb passes to be immobilized by an immobilization system (3) connected to the main strap (2). The thumb immobilization system (3) includes a rod (30) substantially bent into a U-shape to give rise to two end arms (31) which engage telescopically in respective pockets (9, 9') formed on the main strap (2), so as to be able to adjust the thumb immobilizer (3) in position.

11 Claims, 3 Drawing Sheets

FIG. 5
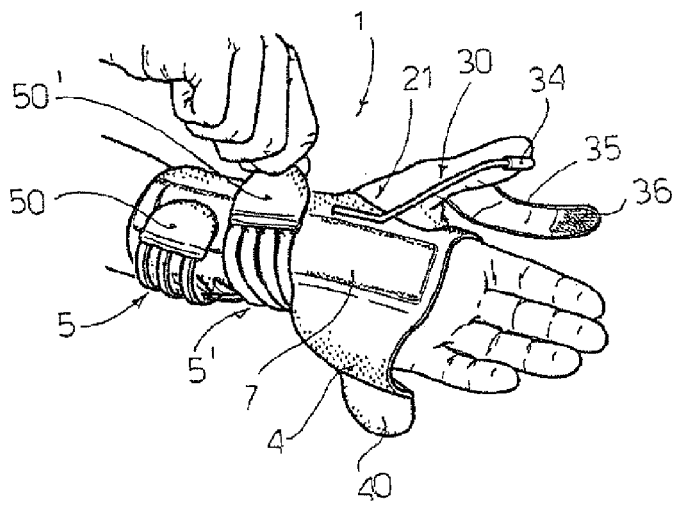
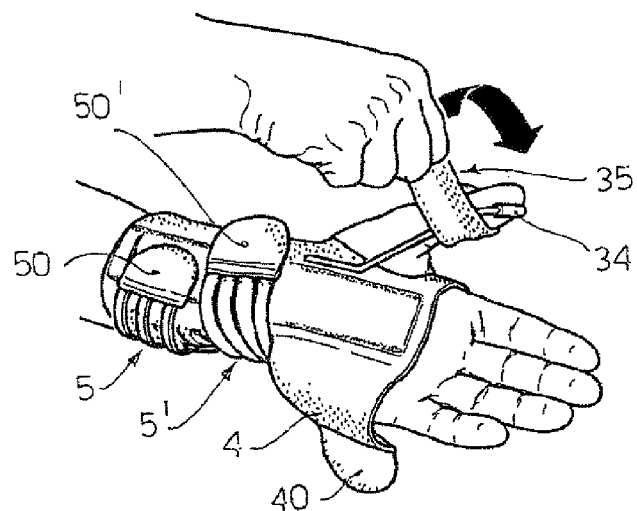
FIG. 6
FIG. 7
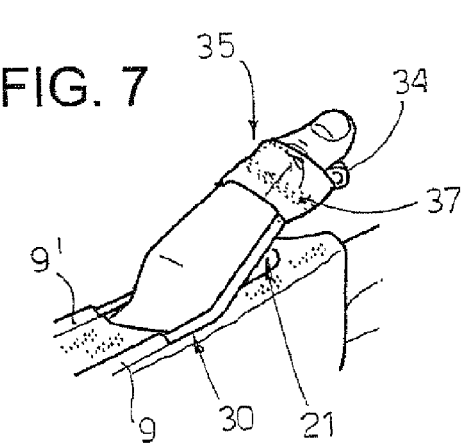
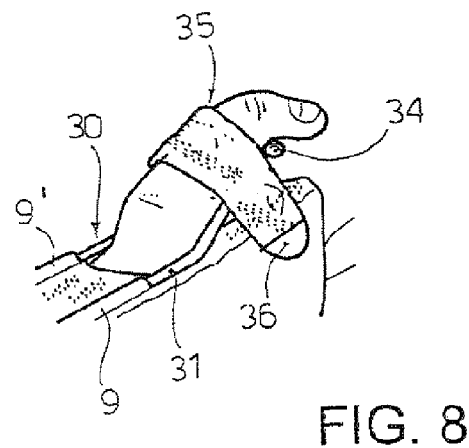
FIG. 8

AMBIDEXTROUS WRIST BRACE WITH THUMB IMMOBILIZER

FIELD OF THE INVENTION

The present invention refers to the field of products for postoperative health and orthopedic use or for rehabilitation. It refers in particular to a brace or support for the wrist provided with a thumb immobilizer.

BACKGROUND OF THE INVENTION

Various types of wrist braces are known on the market, such as for example that described in U.S. Pat. No. 6,893,410. However, such known wrist braces are either lefthand or righthand and present some drawbacks due to their poor fittability and adaptability to the shape of the patient's limb.

In fact, immobilization of the thumb takes place by means of an annular strap which surrounds the thumb, within which a flat rigid rod is placed which runs the whole length of the thumb and the wrist strap. It is obvious that this rod ensures only a complete immobilization, is poorly adaptable to the different traumatological situations of the thumb, is uncomfortable for the patient, does not adapt to the different lengths of the patient's fingers and is not suitable for use after surgical operations since postoperative dressings are present on the patient's thumb, precisely in the position in which the flat rigid rod passes.

Another drawback of wrist braces of the prior art is represented by the fact that they have a tubular shape and must therefore be fitted around the wrist. It is evident that it is difficult for such braces to be fitted in postoperative cases in which dressings are present on the patient's wrist.

SUMMARY OF THE INVENTION

The object of the present invention is to eliminate the drawbacks of the prior art, providing an ambidextrous wrist brace provided with a thumb immobilizer that is extremely comfortable for the patient and at the same time is versatile and adaptable and that can be customized according to the shape of the limb and to the injury suffered by the patient.

Another object of the present invention is to provide such an ambidextrous wrist brace that is particularly suitable to be used after surgical operations, when postoperative wounds are present on the limb.

These objects are achieved according to the invention with the characteristics described below.

Advantageous embodiments of the invention are apparent from the below description.

The wrist brace according to the invention comprises a substantially rectangular main strap, designed to be closed in a tubular shape around the wrist. The main strap has a slot through which the user's thumb passes to be immobilized by an immobilization system connected to the main strap.

The thumb immobilization system comprises a rod substantially bent into a U-shape so as to give rise to two end arms which engage in respective pockets formed on said main strap.

The end arms of the U-shaped rod are advantageously telescopic so as to be able to adjust the thumb immobilization system in position.

This solution presents various advantages of adaptability, comfort and configurability with respect to the prior art.

1) Various types of thumb immobilization can be chosen (for example, a complete immobilization is achieved by inserting the two ends of the rod into the pockets until the curved part of the rod reaches the end of the thumb or a partial immobilization is achieved by inserting the two ends of the rod into the pockets until the curved part of the rod reaches the medial part of the thumb, so that the end of the thumb can move freely, even after blocking with the strap). The arms of the rod can be telescopic to further adapt to patients' different thumb lengths.

2) This immobilization system offers excellent immobilization of the thumb without pressing on the thumb itself with plates, which are often uncomfortable and unbearable because of surgical operations near the base of the thumb.

3) The rod of the immobilization system is supplied with a standard shape, but it can easily be modelled to the size of the patient's thumb by means of further folds.

Moreover the wrist brace according to the invention comprises:
  a substantially rectangular main strap, designed to be closed in the form of a tube around the wrist,
  a plurality of laces having one end integral with on side of said main strap,
  an anchoring strip designed to be fixed on the top surface of the main strap and provided with slots though which said laces pass to be adjusted in position with respect to the main strap, and
  at least one gripping element connected to the other end of said laces and designed to be anchored to the top surface of the main strap, said gripping element being able to be gripped by the user to tension the laces and to close said main strap in a tubular configuration around the wrist.

Said solution makes the wrist brace completely open, that is, the hand does not have to be inserted into the brace, but it is the brace itself that will surround the hand. This facilitates use of the brace in post-operative cases with dressings.

The anchoring strip can be detached from the main strap, making the wrist brace open and increasing size adjustment.

Furthermore the brace according to the invention comprises a substantially rectangular main strap, designed to be closed in a tubular shape around the wrist and provided with a slot through which the user's thumb passes. Pre-prepared cuts, suitable to be cut to remove material and to widen the slot according to requirements, are provided near said slot. This arrangement is particularly suitable for cases in which there are postoperative dressings at the base of the thumb.

BRIEF DESCRIPTION OF THE DRAWINGS

Further characteristics of the invention will be made clearer by the detailed description that follows, referring to a purely exemplary and therefore non-limiting embodiment thereof, illustrated in the appended drawings, in which:

FIG. 5 is a perspective view illustrating the wrist brace according to the invention during tensioning on the user's wrist;

FIG. 6 is a perspective view illustrating the wrist brace according to the invention during the thumb immobilization stage;

FIG. 7 is a perspective view, partially broken off, illustrating the thumb immobilization device in the situation in which the thumb is completely blocked; and FIG. 8 is a perspective view, partially broken off, illustrating the thumb immobilization device in the situation in which the first phalanx of the thumb is free.

DETAILED DESCRIPTION OF EMBODIMENTS

Figure 1:
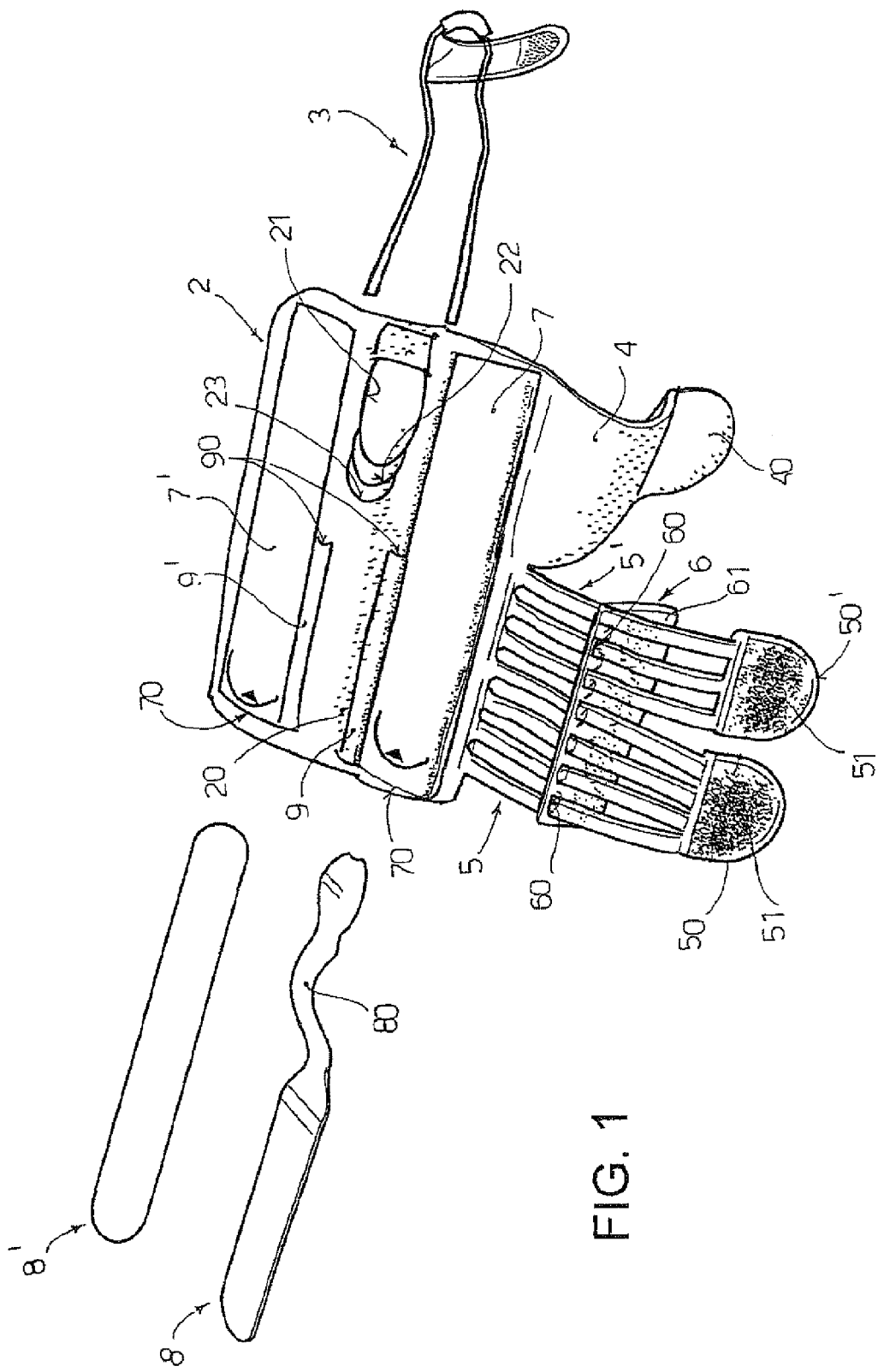
FIG. 1 is a perspective view illustrating, from the side destined to face outwards, the wrist brace according to the invention with the stiffening rods and the thumb immobilization system exploded.

The wrist brace according to the invention, indicated as a whole with reference numeral 1, is described with the aid of the figures.

The wrist brace 1 comprises a main strap 2, substantially rectangular in shape, designed to be closed so as to form a tube, which surrounds the patient's wrist. The main strap 2 is obtained from a multilayer sheet consisting of a plurality of layers of material coupled to one another, preferably by flame bonding.

Said multilayer sheet comprises:
- a bottom layer of anallergic material destined to come into contact with the user's skin,
- a middle padding layer of cushioning, breathable material, for example an open-cell plastic foam material such as polyurethane (PU), and
- an upper layer destined to face outwards, also breathable.

On the upper layer of the main strap 2 there are two pockets (7, 7') having on the outer surface a plurality of loops designed to couple, in an anchoring relationship, with a plurality of complementary hooks of a Velcro-type anchoring element, as will be described hereunder. The upper surface 20 of the main band could also be made of a material suitable to allow a Velcro type coupling or could have portions of material suitable to allow a Velcro type coupling.

The longer sides of the main strap 2 follow the longitudinal direction whilst the shorter sides follow the crosswise direction.

From one side of the main strap 2 protrude transversally a trapezoid-shaped side band 4 and a plurality of rectangular strips or laces (5, 5'), having a greater length and a smaller width than the side band 4. The side band 4 ends with a gripping element 40 suitable to be gripped and tensioned by the user. The gripping element 40 is shaped as a semi-elliptical flap and has an outer surface with a plurality of Velcro-type anchoring elements (hooks) designed to engage with the anchoring elements (loops) of the upper surface of one of the pockets (7, 7') of the strap 2.

The laces (5, 5') are passed through the respective slots 60 formed in a rectangular shaped anchoring strip 6. The anchoring strip 6 has an outer surface 61 provided with Velcro-type anchoring elements (hooks) able to engage with Velcro-type anchoring elements (loops) of the upper surface of one of the pockets (7) of the strap 2. The anchoring strip 6 can slide on the laces (5, 5') to be adjusted in position.

By way of example the laces (5, 5') are seven in number and are divided into a first group 5 of four laces and a second group 5' of three laces. At the free ends of the first group 5 of four laces and of the second group 5' of three laces two respective gripping elements (50, 50'), substantially similar to the gripping element 40 of the side band 4, are fixed. The gripping elements (50, 50') have an outer surface 51 with a plurality of Velcro type anchoring elements (hooks) able to engage with Velcro type anchoring elements (loops) of the upper surface of one of the pockets (7) of the strap 2.

In the median portion of the main strap 2, in front of and coinciding with the side band 4, a slot 21 is formed by blanking, of such a size as to allow the thumb of a hand to be inserted. The slot 21 extends in the longitudinal direction of the main strap 2. Semi-circumferential shaped cuts 22 and 23 designed to be cut with scissors so as to remove material and to enlarge the slot 21 according to requirements are provided alongside the slot 21.

The two longitudinal pockets (7, 7') are attached by sewing on the central portion of the main band 2, on one side and on the other with respect to the slot 21, and extend substantially for the whole length of the main band 2. The pockets (7, 7') have at their rear end respective openings 70 for insertion of the metal rods (8, 8') for stiffening of the structure.

A palmar rod 8 destined to be positioned beneath the palm of the hand and a dorsal rod 8' destined to be positioned on the back of the hand are provided. The palmar rod 8 is shaped as a plate with a curved portion 80 of smaller width destined to surround the palm of the hand. The dorsal rod 8' on the other hand is shaped as a flat, straight plate.

By inverting the position of insertion of the metal rods (the palmar 8 rod and the dorsal rod 8') inside the openings 70 of the pockets 7 and 7', a right or a left wrist support will be obtained.

In order to obtain, for example, a left wrist support, the palmar stiffening rod 8 is inserted in the pocket 7 proximal to the laces (5, 5'), whilst the dorsal stiffing rod 8' is inserted into the pocket 7' distal to the laces (5, 5').

Two smaller pockets (9, 9'), which extend longitudinally for about half the length of the main strap 2 are attached to the rear, median part of the main strap 2 near the pockets (7, 7'). The pockets (9, 9') have at the front respective openings 90 to receive a thumb immobilising system 3.

The pockets 7, 7', 9 and 9' are preferably made of the same material, or in any case of a material suitable to allow a Velcro-type anchoring.

Figure 2:
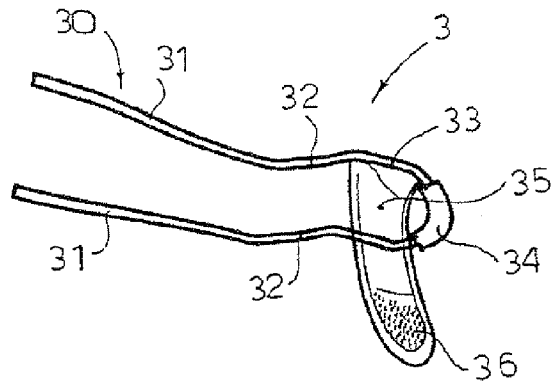
FIG. 2 is an enlarged view of the thumb immobilization system of FIG. 1.

As shown better in FIG. 2, the thumb immobilizing system 3 comprises a rod 30 with a circular section bent substantially in a U shape, so that its ends can be inserted in the pockets (9, 9'). The rod 30 comprises a metal core coated with a plastic material and can be shaped according to requirements.

The rod 30 is suitably shaped to be able to support and to immobilize the user's thumb. The rod 30 comprises, starting from its free ends, two straight arms 31, designed to be inserted in the pockets (9, 9') that continue with two intermediate portions 32 inclined with respect to the arms 31. The inclined intermediate portions 32 are joined with a curved portion 33 lying on a plane substantially parallel to that of the straight arms 31.

Even if not shown in the figures, the arms 31 can have a telescopic length adjustment system to be able to adjust the thumb immobilizing system 3 in position.

A padding of soft material 34 is disposed in the end of the curved portion 33 to receive the tip of the thumb.

Again in the curved portion 33 a strip 35 designed to surround the thumb and to immobilize it to the rod 30 is provided. The strip 35 has at its end a gripping portion 36 designed to be gripped and pulled by the user. The gripping portion 36 has Velcro-type anchoring elements (hooks) designed to engage with complementary anchoring elements (loops) provided on the upper surface 37 (FIG. 7) of the strip 35.

Figure 3:
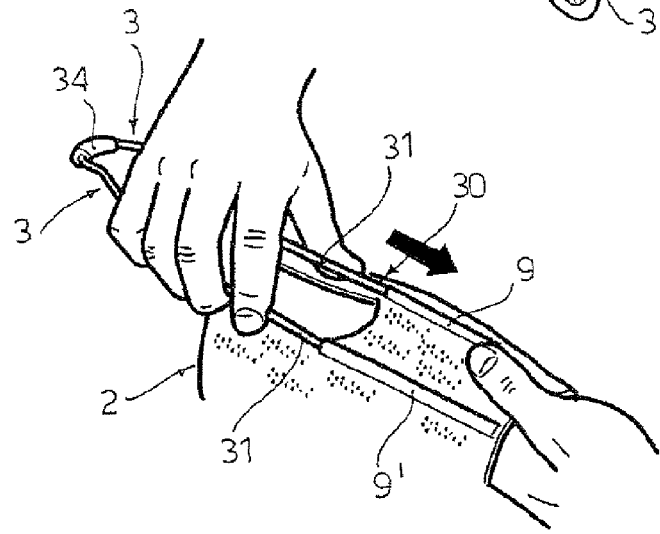
FIG. 3 is a perspective view, partially broken off, illustrating the assembly and the adjustment of the thumb immobilization system.

A shown in FIG. 3 the thumb immobilization system 3 can be adjusted in position according to the length of the patient's thumb, by inserting the straight arms 31 of the rod 30 telescopically into the respective pockets (9, 9').

Figure 4:
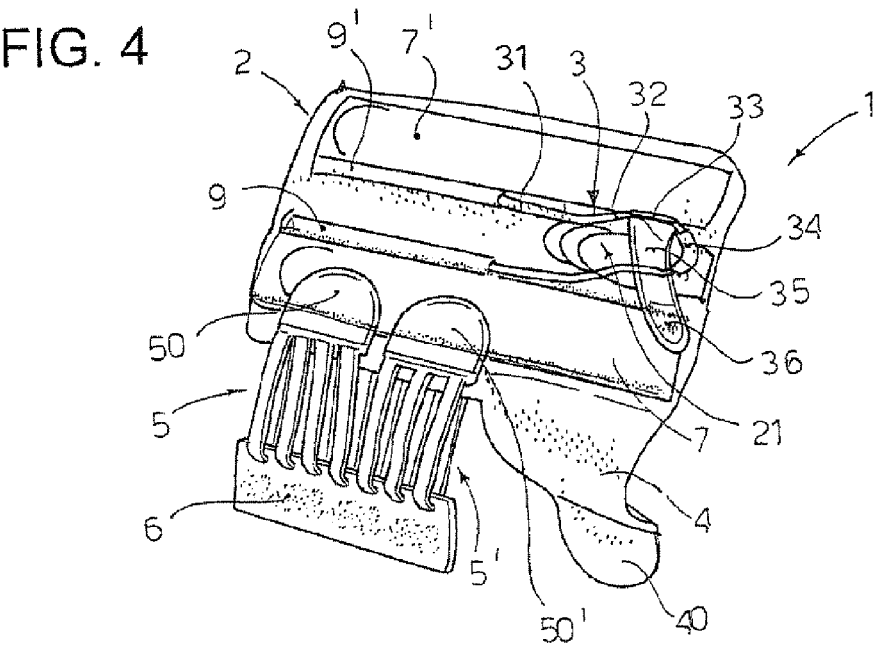
FIG. 4 is a view like FIG. 1, but illustrating the wrist brace assembled and ready to be worn.

In FIG. 4 the brace 1 is illustrated assembled and ready to be worn. In this case the palmar rod 8 and the dorsal rod 8' are inserted in the respective pockets (7, 7') of the main strap, whilst the arms 31 of the rod 30 of the thumb immobilization system 3 are inserted in the respective pockets (9, 9').

In this manner the oblique parts 32 of the rod and the curved joining portion 33 follow the perimeter of the slot 21 for the insertion of the thumb. Moreover the curved portion 33 with its padding 34 is raised with respect to the plane of the main strap 2.

Furthermore the gripping elements (50, 50') connected to the laces (5, 5') are fixed on the upper surface of the main strap 2, coinciding with the pocket 7. The anchoring strip 6, on the other hand, remains detached from the main strap 2.

As shown in FIG. 5, the brace 1 is fitted on the user's wrist so that the thumb of the hand enters the slot 21 of the brace and the tip of the thumb rests on the padding 34 of the rod 30 of the thumb immobilization system 3.

Then, the user takes the anchoring strip 6 with the other hand and anchors it on the upper surface of the main strap 2, substantially coinciding with the pocket 7', so as to surround the wrist with the main strap 2 and the laces (5, 5').

Subsequently the user grips the first gripping element 50 so as to tension the group 5 of four laces as much as possible and then blocks the gripping element 50 on the upper surface of the main strap 2 coinciding with the pocket 7; then he grips the second gripping element 50' so as to tension the group 5' of three laces as much as possible and then blocks the gripping element 50' on the upper surface of the main band 2 coinciding with the pocket 7.

With reference to FIG. 6, the user grips the gripping part 36 of the strip 35 of the thumb immobilization system and turns the strip 35 around the thumb, so as to immobilize the thumb on the rod 30, then blocks the gripping part 36 on the outer surface of the strip 35.

Finally the user grips the third gripping element 40 so as to tension the side band 4 as much as possible and then blocks the gripping element 40 on the upper surface of the main strap 2 coinciding with the pocket 7'.

It should be noted that, during the application of the brace 1, the bottom surface of the laces (5, 5') can come into contact with the user's skin; this does not prove to be a problem since the bottom surface of the laces is made of the same anallergic material as the bottom surface of the main strap 2.

It should be noted that thanks to the possibility of adjusting the position of the immobilization system 3, it is possible to obtain a complete or a partial immobilization of the thumb.

FIG. 7 illustrates the situation in which the padding 34 of the curved end of the rod 30 is situated beneath the tip of the thumb and the strip 35 completely surrounds the thumb, completely immobilizing it.

FIG. 8 on the other hand illustrates the situation in which the padding 34 of the curved end of the rod 30 is situated beneath the joint between the first and the second phalanx of the thumb. Thus in this case the first phalanx of the thumb is not immobilized and can move.

Numerous variations and modifications of detail within the reach of a person skilled in the art can be made to the present embodiment of the invention without thereby departing from the scope of the invention as set forth in the appended claims.

The invention claimed is:

1. A wrist brace (1) comprising a substantially rectangular main strap (2), designed to be closed like a tube around the wrist and provided with a slot (21) through which the user's thumb passes to be immobilized by an immobilization system (3) connected to the main strap (2),
wherein said thumb immobilization system (3) comprises a rod (30) bent substantially in a U-shape so as to give rise to two end arms (31) which engage in respective pockets (9, 9') formed on said main strap (2), and
wherein said end arms (31) have a telescopic length adjustment system, so as to be able to adjust said thumb immobilization system (3) in position.

2. The wrist brace (1) according claim 1, wherein said thumb immobilization system (3) comprises a strip (35) having one end connected to said rod (30) and designed to surround the thumb to immobilize it the thumb on said rod (30).

3. The wrist brace (1) according to claim 2, wherein said strip (35) of the thumb immobilization system (3) comprises at a free end a gripping portion (36) designed to be gripped and pulled by the user, said gripping portion being provided with Velcro type anchoring elements, designed to engage with complementary anchoring elements provided on the strip (35) or on the main strap (2).

4. The wrist brace (1) according to claim 1, wherein in said main strap (2), near said slot (21) for the passage of the thumb, there are provided pre-prepared cuts (22, 23) designed to be cut to remove material and to enlarge the slot (21) according to requirements.

5. A wrist brace comprising a substantially rectangular main strap (2), designed to be closed like a tube around the wrist and provided with a slot (21) through which the user's thumb passes to be immobilized by an immobilization system (3) connected to the main strap (2),
wherein said thumb immobilization system (3) comprises a rod (30) bent substantially in a U-shape so as to give rise to two end arms (31) which engage in respective pockets (9, 9') formed on said main strap (2), and
wherein said rod (30) of the thumb immobilization system (3) has a substantially circular section, comprises a metal core coated with plastic material and can be suitably shaped, according to requirements.

6. A wrist brace comprising a substantially rectangular main strap (2), designed to be closed like a tube around the wrist and provided with a slot (21) through which the user's thumb passes to be immobilized by an immobilization system (3) connected to the main strap (2),
wherein said thumb immobilization system (3) comprises a rod (30) bent substantially in a U-shape so as to give rise to two end arms (31) which engage in respective pockets (9, 9') formed on said main strap (2), and
wherein said rod (30) of the thumb immobilization system (3) comprises two straight arms (31), which continue with two inclined portions (32), which are joined with a curved portion (33).

7. A wrist brace comprising a substantially rectangular main strap (2), designed to be closed like a tube around the wrist and provided with a slot (21) through which the user's thumb passes to be immobilized by an immobilization system (3) connected to the main strap (2),
wherein said thumb immobilization system (3) comprises a rod (30) bent substantially in a U-shape so as to give rise to two end arms (31) which engage in respective pockets (9, 9') formed on said main strap (2), and
wherein on the curved portion (33) of said rod (30) of the thumb immobilization system there is disposed a padding (34) of soft material, to support a part of the tip of the thumb.

8. A wrist brace comprising a substantially rectangular main strap (2), designed to be closed like a tube around the wrist and provided with a slot (21) through which the user's thumb passes to be immobilized by an immobilization system (3) connected to the main strap (2),
wherein said thumb immobilization system (3) comprises a rod (30) bent substantially in a U-shape so as to give rise to two end arms (31) which engage in respective pockets (9, 9') formed on said main strap (2), and said wrist brace further comprises:

a plurality of laces (5, 5') having one end integral with one side of said main strap (2), an anchoring strip (6) designed to be fixed to the upper surface (20) of the main strap (2) or on pockets (7, 7') disposed on said upper surface (20) and provided with slots (60) through which said laces (5, 5') pass to be adjusted in position with respect to the mains strap (2), and at least one gripping element (50, 50') connected to the other end of said laces (5, 5') and designed to be fixed to the upper surface (20) of the main strap (2) or on pockets (7, 7') disposed on said upper surface (20), said gripping element (50, 50') being able to be gripped by the user to tension the laces (5, 5') and to close said main strap (2) in a tubular shape around the wrist.

9. The wrist brace (1) according to claim 8, wherein on said main strap (2) there are formed two longitudinal pockets (7, 7') disposed substantially in a symmetrical position with respect to a midline, to receive a palmar stiffening rod (8), flat and slightly curved to be disposed beneath the palm of the hand, and a dorsal stiffening rod (8'), flat and straight to be disposed on the back of the hand, said palmar and dorsal rods (8, 8') being interchangeable, to be able to give rise to an ambidextrous brace.

10. A wrist brace (1) comprising:

a substantially rectangular main strap (2), designed to be closed in a tubular shape around the wrist, a plurality of laces (5, 5') having one end integral with one side of said main strap (2), an anchoring strip (6) designed to be fixed on the upper surface (20) of the main strap (2) or on pockets (7, 7') disposed on said upper surface (20) and provided with slots (60) through which said laces (5, 5') pass to be adjusted in position with respect to the main strap (2), said slots are formed through the material of said anchoring strip and at least one gripping element (50, 50') connected to the other end of said laces (5, 5') and designed to be fixed to the upper surface (20) of the main strap (2) or on pockets (7, 7') disposed on said upper surface (20), said gripping element (50, 50') being able to be gripped by the user to tension the laces (5, 5') and to close said main strap (2) in a tubular configuration around the wrist.

11. A wrist brace comprising a substantially rectangular main strap (2), designed to be closed like a tube around the wrist and provided with a slot (21) through which the user's thumb passes to be immobilized by an immobilization system (3) connected to the main strap (2), wherein said thumb immobilization system (3) comprises a rod (30) bent substantially in a U-shape so as to give rise to two end arms (31) which engage in respective pockets (9, 9') formed on said main strap (2), and wherein on said main strap (2) there are formed two longitudinal pockets (7, 7') disposed substantially in a symmetrical position with respect to a midline, to receive a palmar stiffening rod (8), flat and slightly curved to be disposed beneath the palm of the hand, and a dorsal stiffening rod (8'), flat and straight to be disposed on the back of the hand, said palmar and dorsal rods (8, 8') being interchangeable, to be able to give rise to an ambidextrous brace.

* * * * *